United States Patent
Cui et al.

(10) Patent No.: US 8,816,292 B2
(45) Date of Patent: Aug. 26, 2014

(54) COMPACT ENDOCAVITY DIAGNOSTIC PROBES FOR NUCLEAR RADIATION DETECTION

(75) Inventors: Yonggang Cui, Miller Place, NY (US); Ralph James, Ridge, NY (US); Aleksey Bolotnikov, South Setauket, NY (US)

(73) Assignee: Hybridyne Imaging Technologies, Inc., Toronto, Ontario (CA)

( * ) Notice: Subject to any disclaimer, the term of this patent is extended or adjusted under 35 U.S.C. 154(b) by 262 days.

(21) Appl. No.: 13/077,627

(22) Filed: Mar. 31, 2011

(65) Prior Publication Data

US 2011/0286576 A1   Nov. 24, 2011

Related U.S. Application Data

(60) Provisional application No. 61/320,157, filed on Apr. 1, 2010.

(51) Int. Cl.
*G01T 1/00* (2006.01)
*A61B 17/94* (2006.01)

(52) U.S. Cl.
USPC .................................................. 250/370.09

(58) Field of Classification Search
USPC ............... 250/336.1, 370.01, 370.08, 370.09; 600/407, 431, 436
See application file for complete search history.

(56) References Cited

U.S. PATENT DOCUMENTS

| | | | |
|---|---|---|---|
| 3,011,057 A | 11/1961 | Anger | |
| 4,015,592 A | 4/1977 | Bradley-Moore | |
| 4,595,014 A * | 6/1986 | Barrett et al. | 600/431 |
| 4,995,396 A * | 2/1991 | Inaba et al. | 600/431 |
| 5,008,546 A * | 4/1991 | Mazziotta et al. | 250/366 |
| 5,014,708 A * | 5/1991 | Hayashi et al. | 600/436 |
| 5,088,492 A * | 2/1992 | Takayama et al. | 600/431 |
| 5,119,818 A * | 6/1992 | Carroll et al. | 600/436 |
| 5,170,055 A * | 12/1992 | Carroll et al. | 250/336.1 |
| 5,245,191 A | 9/1993 | Barber et al. | |
| 5,444,254 A * | 8/1995 | Thomson | 250/370.07 |
| 5,732,704 A | 3/1998 | Thurston et al. | |
| 5,846,513 A * | 12/1998 | Carroll et al. | 424/1.11 |
| 5,847,398 A | 12/1998 | Shahar et al. | |
| 6,037,595 A | 3/2000 | Lingren et al. | |
| 6,175,120 B1 | 1/2001 | McGregor et al. | |
| 6,218,669 B1 * | 4/2001 | Call | 250/370.11 |
| 6,222,193 B1 | 4/2001 | Thurston et al. | |

(Continued)

FOREIGN PATENT DOCUMENTS

WO   WO 99/61880 A2   12/1999
WO   WO 2008/149362 A3   12/2008

OTHER PUBLICATIONS

Barrett, H., et al., "Charge transport in arrays of semiconductor gamma-ray detectors," *Phys. Rev. Lett.*, 75 (1), pp. 156-159, (1995).

(Continued)

*Primary Examiner* — Mark R Gaworecki
(74) *Attorney, Agent, or Firm* — Charles N. Quinn; Fox Rothschild LLP

(57) ABSTRACT

This invention relates to the field of radiation imaging. In particular, the invention relates to an apparatus and a method for imaging tissue or an inanimate object using a novel probe that has an integrated solid-state semiconductor detector and complete readout electronics circuitry.

10 Claims, 12 Drawing Sheets

(56) References Cited

U.S. PATENT DOCUMENTS

| | | | |
|---|---|---|---|
| 6,495,834 | B1 | 12/2002 | Corvo et al. |
| 6,524,966 | B1 | 2/2003 | Wright et al. |
| 6,602,488 | B1 | 8/2003 | Daghighian |
| 6,643,538 | B1 | 11/2003 | Majewski et al. |
| 6,940,070 | B2 | 9/2005 | Tümer |
| 7,001,849 | B2 | 2/2006 | Wright et al. |
| 7,634,061 | B1 | 12/2009 | Tümer et al. |
| 7,847,261 | B2 * | 12/2010 | Tomita et al. ............ 250/370.11 |
| 2003/0081716 | A1 * | 5/2003 | Tumer .............................. 378/19 |
| 2004/0061059 | A1 * | 4/2004 | Gobel et al. ............. 250/370.01 |
| 2009/0026371 | A1 | 1/2009 | Bolotnikov et al. |
| 2010/0010343 | A1 | 1/2010 | Daghighian et al. |
| 2010/0156644 | A1 * | 6/2010 | Tomita et al. ................. 340/600 |

OTHER PUBLICATIONS

Bolotnikov, A., et al., "Optimization of virtual Frisch-grid CdZnTe detector designs for imaging and spectroscopy of gamma rays," in Hard X-ray and Gamma-Ray Detector Physics IX, edited by James, R., et al., *Proc. SPIE*, 6706, pp. 670603-1 to 670603-14, (SPIE Bellingham, WA, 2007).

Lund, J., et al., "Miniature Gamma-Ray Camera for Tumor Localization," [online] issued by *Sandia National Laboratories*, Aug. 1997 [retrieved on Mar. 31, 2011] retrieved from the internet: <URL: http://www.osti.gov/energycitations/purl.cover.jsp?purl=/555271-KYNEJ1/webviewable/> pp. 1-30.

Lund, J., et al., "Miniature Gamma-Ray Camera for Tumor Localization," [online] issued by *Sandia National Laboratories*, Aug. 1997 [retrieved on Mar. 31, 2011] retrieved from the internet: <URL: http://www.osti.gov/energycitations/purl.cover.jsp?purl=/555271-KYNEJ1/webviewable/> pp. 31-62.

Montemont, G., et al., "A capacitive Frisch grid structure for CdZnTe detectors," *IEEE Trans. Nucl. Sci*, 48, (3), pp. 278-281, (2001).

Parnham, K., et al., "Performance improvement of CdZnTe detectors using modified two-terminal electrode geometry," in Hard X-Ray, Gamma-Ray and Neutron Detector Physics, *Proceedings of SPIE*, 3768, pp. 49-54 (SPIE Denver, CO, 1999).

Szeles, C., et al., "Fabrication of high performance CdZnTe quasi-hemispherical gamma-ray CAPture Plus detectors," in Hard X-Ray and Gamma-Ray Detector Physics VIII, edited by Franks, et al., *Proceedings of SPIE*, 6319 pp. 191-198, (SPIE, Bellingham, WA, 2006).

Williams, M., et al., "Investigation of spatial resolution and efficiency using pinholes with small pinhole angle," *IEEE TNS/MIC*, 3, pp. 1760-1764, (2002).

* cited by examiner

COMPACT ENDOCAVITY DIAGNOSTIC PROBES FOR NUCLEAR RADIATION DETECTION

CROSS-REFERENCE TO RELATED APPLICATIONS

This application claims the benefit of U.S. Provisional Application No. 61/320,157, filed Apr. 1, 2010, which is incorporated herein by reference in its entirety.

STATEMENT OF GOVERNMENT RIGHTS

This invention was made with Government support under contract number DE-AC02-98CH10886, awarded by the U.S. Department of Energy. The Government has certain rights in the invention.

I. FIELD OF THE INVENTION

This invention relates to the field of radiation imaging. In particular, the invention relates to an apparatus and a method for imaging tissue, such as the colon and prostate, or an inanimate object using a novel probe that has an integrated solid-state semiconductor detector and a complete readout electronics circuitry.

II. BACKGROUND OF THE RELATED ART

In medical imaging applications, two competing technologies are generally used: ultrasound and nuclear medical imaging. The benefit of the ultrasound technology is that it enables a very compact design of a probe that is powerful in revealing the anatomical structures of the organs. However, ultrasound technology is not an ideal tool in cancer detection and diagnosis because ultrasound can only generate anatomical images, whereas functional images are needed, especially at the early stages of cancer. For example, in prostate cancer diagnosis, the ultrasound probe produces and subsequently records high-frequency sound waves that bounce off the prostate's surface, and transforms the recorded sound waves into video or photographic images of the prostate gland. The probe generates images at different angles to help the physician estimate the size of the prostate and detect abnormal growths; however, benign and cancerous tumors cannot easily be distinguished by ultrasound. In addition, if the patient had radiation treatment in or around the prostate before, the fibrous tissues can be mistakenly identified as tumors during the interpretation of the sonograms. Hence, while the ultrasound probes can be designed to be very compact and easy to carry, handle, and operate, their inability to distinguish benign and cancerous tumors makes them unsuitable for functional imaging required in cancer imaging and diagnosis.

By contrast, the traditional diagnostic nuclear medical imaging techniques have the capacity to provide the desirable functional images. Such methods use radioactive tracers, short-lived isotopes that emit gamma rays from within the body and are linked to chemical compounds, permitting the characterization of specific physiological processes. The isotopes can be given by injection, inhalation, or by mouth. Normally an imaging device (e.g., Anger gamma camera as described in U.S. Pat. No. 3,011,057, which is incorporated herein by reference in its entirety) is used to image single photons emitted from an organ. The camera builds up an image of the points where radiation is emitted. This image is then enhanced by a computer, projected on a monitor, and viewed by a physician for indications of cancer. Exemplary commercial nuclear imaging systems that are capable of producing functional images include PET (Positron Emission Tomography) and SPECT (Single Photon Emission Computerized Tomography). Some of these systems are based on scintillator detectors, such as NaI, CsI and BGO, plus photon sensing devices, such as photomultipliers or photodiodes (see, e.g., U.S. Pat. No. 5,732,704, incorporated herein by reference in its entirety). Other systems are based on high-purity germanium (HPGe) crystals. Although HPGe itself is small, it needs a complex cooling system to work at cryogenic temperatures (e.g., −180° C.). Hence, all of these systems, either based on scintillator detectors or HPGe crystals, are bulky and can only be integrated into an external detection system. However, since the detectors of such external systems are located far away from the imaged organs, they have poor detection efficiency and low spatial resolution, which limit such detector's ability to pinpoint the exact positions of cancerous tissues in a small organ. All these drawbacks limit the usefulness of such radiation detection systems in diagnosing cancer in small organs, e.g. prostate glands, particularly for small tumors.

In view of the foregoing problems and drawbacks encountered in the conventional diagnostic techniques, it is highly desirable to develop a new device that would offer compact size, higher spatial resolution, and higher detection efficiency, and to provide a system with high accuracy in diagnosing cancers in small organs, e.g. prostate glands.

SUMMARY OF THE INVENTION

In accordance with the present invention, a novel radiation imaging probe comprising a plurality of semiconductor radiation detectors, complete signal processing circuitry, and a power supply within a cylindrical sheath is disclosed. More particularly, the semiconductor radiation detector within the radiation imaging probe of the present invention is preferably based on solid state semiconductors capable of operating as photon-charge direct conversion devices arranged as a radiation imaging camera that can localize the distribution variations of radiation sources in tissues or inanimate objects. We recognized that the novel radiation imaging probe based on the solid-state semiconductor detector of the present invention has unique features that ensure high image contrast, high spatial resolution, and high image quality, suitable for gamma ray and X-ray imaging. Moreover, with the highly integrated signal processing circuits and the readout control logic, the probe of the present invention can be designed to be very compact and easy to carry, handle, and operate. Alternatively, the probe of the present invention may have dual functionality by incorporating a radiation imaging module(s) and the ultrasound modules: one detecting radiation to produce a functional image and the other to simultaneously produce an anatomical image.

The radiation imaging probe of the present invention, enclosed in a cylindrical sheath, has one end sealed, and the other end open to allow for connection between the probe and a computer for further processing and visualization. The main part of the radiation imaging probe is defined by a detector module that, preferably, comprises a plurality of semiconductor radiation detectors with a specific electrode configuration for imaging. One of such configurations is a pixilated detector. It has one common cathode on one side, and an array of anodes on the other side. Each anode is read out separately to provide 2-D spatial information. Another one of such configurations is an array of individual detectors. Each individual detector can be a planar detector, virtual Frisch-grid detector, or other similar bar-shaped detectors. Each element is fabricated separately, and all the elements are integrated into an array. Similarly to the pixilated detector, each anode in the array is read out separately to provide 2-D spatial information. A further configuration may include a cross-strip detector. A cross-strip detector has one set of linear arrays of electrodes on one side, and another set of linear arrays of electrodes on the other side, oriented perpendicular to the direction of the former array. In this configuration, signals are read out from both sides. Coincidence of signals from these two sets of arrays indicates the interaction position of the gamma-ray or x-ray photon inside the detector, thus providing 2-D spatial information.

The semiconductor radiation detector within the radiation imaging probe of the present invention is preferably fabricated from a solid state semiconductor capable of operating as photon-charge direct conversion device. In particular, such semiconductors may be derived from, but not limited to, elements of groups III and V, e.g. GaAs, groups II and VI, e.g. CdTe, and group IV, e.g., Si, of the periodic table. Among these semiconductors and their alloys, cadmium telluride (CdTe), cadmium zinc telluride (CdZnTe), cadmium manganese telluride (CdMnTe), thallium bromide (TlBr), mercury iodide ($HgI_2$), or silicon (Si) may be used, while cadmium zinc telluride (CdZnTe) is the most preferred. The detector is preferably operable at body temperature without the need for cooling.

The detector module of the present invention may be further defined by a collimator positioned on top of the plurality of semiconductor radiation detectors. The collimator is fabricated from a radiation-absorbing material that has a high density and a moderate to high atomic mass. Examples of such materials include, but are not limited to, lead (Pb), tungsten (W), gold (Au), molybdenum (Mo), and copper (Cu). The selection of the radiation-absorbing material and the thickness of the radiation-absorbent material should be determined so as to provide efficient absorption of the incident radiation, and would normally depend on the type of incident radiation and the energy level of the radiation when it strikes the surface plane of the collimator. The type of incident radiation and the energy level of the radiation depends on the particular imaging application, e.g., medical or industrial, or may be designed to be used in any of several different applications by using a general purpose radiation-absorbing material. The basic design of the collimator includes a plurality of parallel apertures with their axes perpendicular to the surface of the collimator. In addition, the collimator may have a special pattern of apertures for specific applications. For example, the collimator can have a fan-beam pattern of apertures, which brings a larger field-of-view to the system, or a focus pattern of apertures, which gives higher spatial resolution as the collimator magnifies the imaged tissue. The collimator may also have a plurality of apertures in one predefined angle or orientation interleaved with a plurality of apertures in another predefined angle to give multiple discrete orientations that may be observed by the detector of the present invention. Alternatively, the collimator can be eliminated, and gamma images can be produced by tracking multiple Compton scattered events in coincidence within the detector, and then using a Compton reconstruction scheme to produce the final image.

The detector module of the present invention may be further defined by shielding surrounding the detector and the collimator. While it is also envisioned, in one embodiment, that the detector module is left unshielded, preferably a side shielding surrounds the four side surfaces of the detector and the collimator and even more preferably, in addition to the side shielding, a back shielding is also implemented to fully cover the detector from all directions except that of the object of interest. The composition of the shielding is not limited to any particular compound and may be made in accordance with what is known in the art. The shape of the shield may be rectangular, circular, or the like. In fact, without being bound by a theory, it is anticipated that circular shielding may provide an advantage because it can easily fit into the sheath of the probe and better shield the detector due to a greater thickness of shielding material between the sheath and the detector.

The semiconductor radiation imaging probe of the present invention may be further defined by the front-end electronics (also referred to as signal processing circuits) that can be implemented, for example, in an application-specific integrated circuit (ASIC) or using commercial circuits plus discrete components, such as a FPGA, a Microcontroller/Microprocessor, or a combination thereof. In addition to the front-end electronics, there are also readout control logic circuits to read out data from the front-end electronics and power supplies (both low voltage for the signal processing circuits and high voltage for the semiconductor radiation detector biasing), which are integrated into the probe. The front-end electronics can be mounted side-by-side with the detectors on the same side of a printed circuit board (PCB), or underneath the semiconductor radiation detectors on the other side of the PCB. Alternatively, the system integration can have all the circuits on different boards as long as all these boards are integrated together into one probe sheath. In yet another alternative, the system integration can have all the circuits on different boards in multiple interconnected units, where the detector module and the signal processing circuits are integrated on one PCB in one probe sheath, while the rest of the circuitry, e.g., power circuitry, is integrated in a separate unit connected to the probe. When the front-end electronics are implemented in an ASIC, the plurality of radiation detectors can be mounted directly on the ASIC instead of on the PCB. Connections between the semiconductor detector and ASIC can use bump-bonding technology while the connections between ASIC and PCB can use wire-bonding.

BRIEF DESCRIPTION OF THE DRAWINGS

FIG. 9A illustrates the source position before the movement and FIG. 9B illustrates the source position after the movement.

DETAILED DESCRIPTION

Figure 1A:
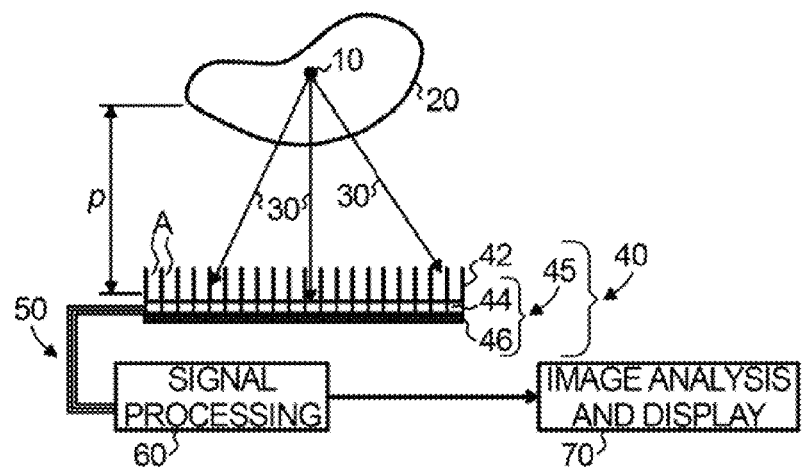
FIG. 1A illustrates an imaging process of the probe of the present invention.

The present invention is directed to a novel radiation imaging probe that offers a compact size that is easy to carry, handle, and operate, and exhibits high energy resolution and detection efficiency. In the following detailed description of the preferred embodiments and various examples of the probe according to the present invention, reference is made to the accompanying drawings where like reference numerals refer to like parts. The drawings illustrate various embodiments in which a hybrid probe for radiation imaging applications may be practiced. It is to be understood, however, that those skilled in the art may develop other structural and functional modifications without significantly departing from the scope of the instant disclosure.

Figure 2A:
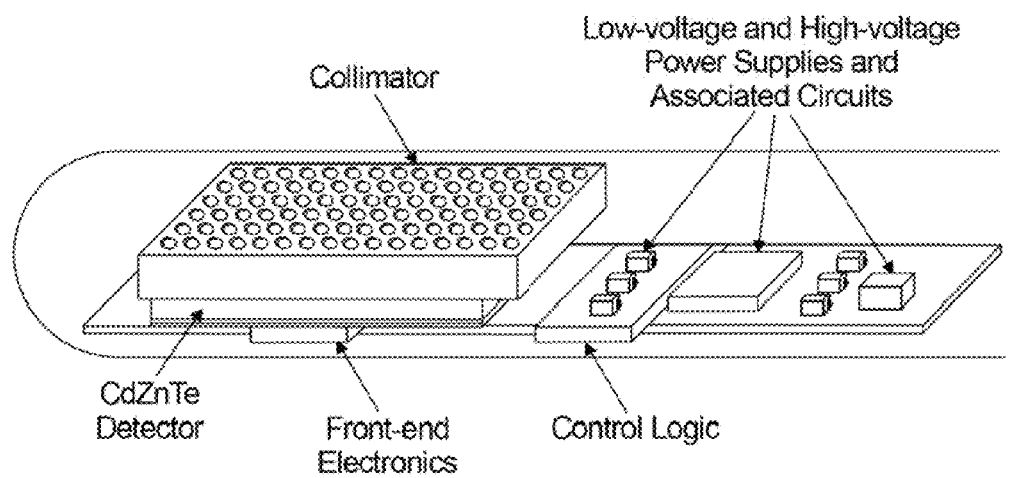
FIG. 2A illustrates an exemplary embodiment of the endocavity diagnostic probe of the present invention with one board hosting all the circuits.
Figure 2B:
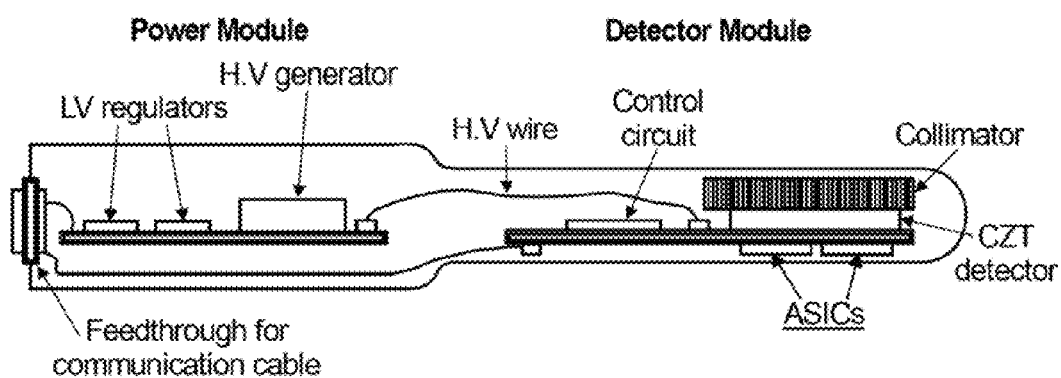
FIG. 2B illustrates an exemplary embodiment of the probe with two separate boards hosting the circuits.

FIG. 2A and FIG. 2B illustrate two embodiments of the radiation imaging probe of the present invention. The probe is encapsulated within a tube (sheath or sleeve) and includes a detector module and a collimator. The collimator is fabricated of a radiation absorbing material and includes a plurality of closely arranged apertures, e.g., parallel holes or pinholes. The detector module is arranged parallel to the collimator, and includes a plurality of radiation detector elements. The radiation detector elements are arranged in a one- or two-dimensional array, preferably in a two-dimensional array, atop a mounting frame board, e.g., a PCB, and connected to signal processing circuits (or front-end electronics; e.g., an ASIC) to read out the signal from the plurality of radiation detector elements. The signal processing circuit(s) is connected to a control logic unit to read out data from the signal processing circuit(s), and power supply circuitry to read out data from the power supply. The configuration and components of the radiation imaging probe of the present invention are discussed in detail below.

I. GENERAL PARAMETERS OF THE PROBE

In the radiation imaging system of the present invention (for examples see FIGS. 1A and 4), the probe allows for an object placed at a predetermined distance from the radiation detection device to be imaged. The overall size of the probe and the material used to produce the sheath of the probe depend on the particular imaging application, e.g., medical, industrial, or security, or may be chosen to be used in any of several different applications by using general purpose materials. The sheath has one end sealed, and the other end open to allow for connection between the probe, that incorporates the detector module and the power module, and a computer for further processing and visualization. Alternatively, the probe that incorporates only the detector module is connected to another processing unit with the power module and subsequently to a computer.

The shape of the probe may be cylindrical, rectangular prismatic, rectangular prismatic with soft edges, or any other shape. In medical applications, for comfort any elongated shape may be utilized as long as it does not have any sharp edges, unless the instrument is also used as a cutting tool for surgery. The probe further should be sufficiently small to allow for an endocavity insertion. For easy operation, the probe may have different sizes (different diameters in case of cylindrical shape) for the sealed end and the open end. For example, the open end, as a handle, may be bigger. The probe may have various lengths depending on the depth of the cavity into which the probe will be inserted. On the other hand, the diameter of the probe is between about 5 mm to about 25 mm. In a more preferred embodiment, the diameter of the probe is between about 6 mm to about 14 mm. In the most preferred embodiment, the diameter of the probe is about 12 mm. In the most preferred embodiment, the volume of the probe is about $30(L) \times 2.5(W) \times 2.5(H)$ cm$^3$. Finally, the weight must be minimized for manual handling or articulating arms may provide counterbalancing for placement. In one embodiment, the probe weighs less than 2 kg, however, in a preferred embodiment, the probe may weigh less than about 500 g. In order to minimize the weight of the probe, it is important that the material used to construct the sheath is lightweight and does not interfere with the detection/imaging of the probe. Hence, the sheath is fabricated from a radiation-transparent material that has low density and/or low atomic mass, and absorbs little or no radiation in the spectral region of interest. Examples of such materials include, but are not limited to, carbon (C; e.g., plastics and other polycarbonates), aluminum (Al), stainless steel, and the like. The selection of the sheath material and the thickness of this material should be determined so as to provide efficient pass of the incident radiation, and would normally depend on the type of incident radiation and the energy level of the radiation. Alternatively, while the overall body of the sheath may be made of one non-optimal, although lightweight material, the portion of the sheath above the collimator may be made from different more desirable radiation—transparent material.

Figure 4:
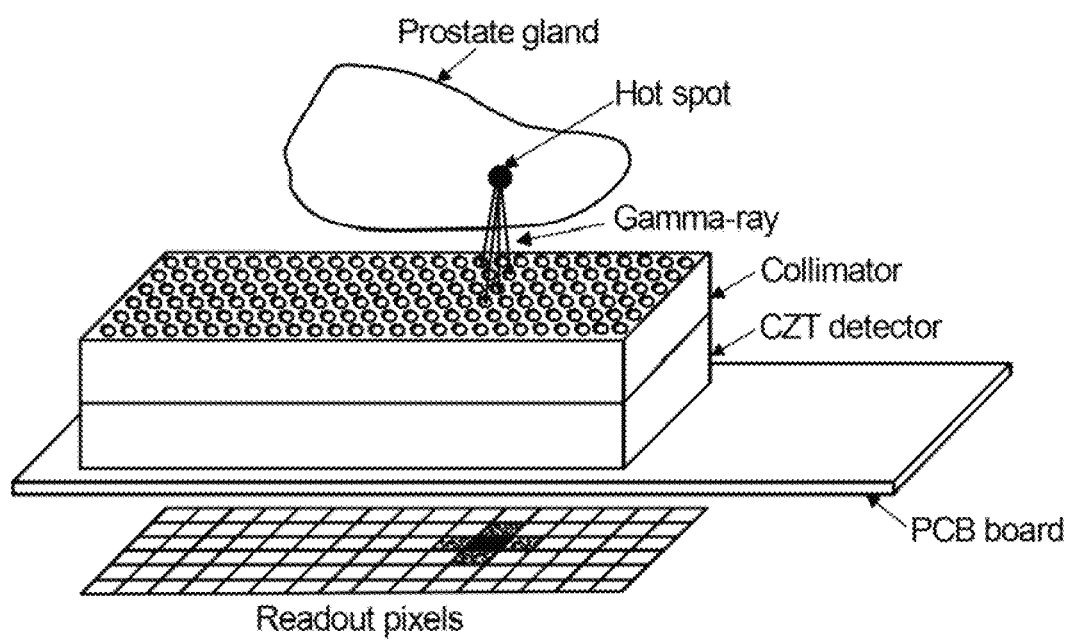
FIG. 4 illustrates an imaging process of the probe of the present invention.

FIG. 1A and FIG. 4 show how the probe works. Assuming a hot spot 10, e.g., cancerous tissue, is inside the imaged organ 20 (illustrated as a prostate gland in FIG. 4), when radiopharmaceuticals are administrated into patient's body, the radioactive tracer will concentrate in the specific damaged or abnormal tissues (illustrated as a hot spot in FIG. 4) inside the target organ. The tracer will decay and emit gamma-ray photons in all directions with known energy (e.g. 140 keV gamma rays for Tc-99m, 27-36 keV gamma rays for 1-125, 171 keV and 245 keV gamma rays for 1n-111, 364 keV gamma rays for I-131). Only the photons 30 with trajectories parallel to the axis of the collimator 42 apertures A can reach the radiation detector 45. Alternatively, the collimator can be eliminated, and gamma images can be produced by tracking multiple Compton scattered events in coincidence within the detector and then using a Compton reconstruction scheme to produce the final image. These photons will ionize the compound semiconductor and generate electron-hole pairs that are separated and guided to the contacts by the internal electric field. The number of pairs generated by a photon is proportional to the photon's energy. Because the compound semiconductor detector is negatively biased, the electrons will drift to the anodes (pixels) while the holes will drift to the cathode. The amplitude of this signal is proportional to the energy of the gamma-ray photon, and can be processed and read out by the front-end electronics and the control logic. Essentially, the front-end electronics counts the photon absorption events within each pixel of the detector. With the guidance of the collimator 42, the region right underneath the hot spot 10 has the highest counts. The accumulated result is a projection of the hot spot on the plane parallel to the detector surface.

II. THE DETECTOR MODULE

Figure 8:
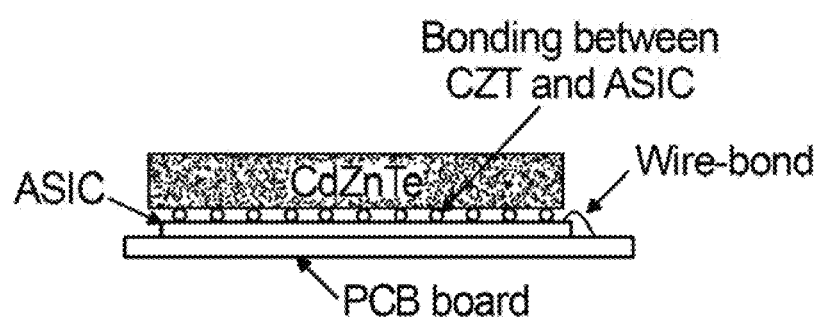
FIG. 8 illustrates an exemplary embodiment of mounting the radiation detector to an ASIC using a bump-bonding technique.

In one embodiment of the radiation imaging system 40 of the present invention (for examples see FIGS. 1A), the detector module 45 includes a plurality of radiation detector elements 44. The radiation detector elements 44 are arranged in a one or two-dimensional array atop a mounting frame board 46, e.g., a PCB, and provide direct conversion of detected radiation energy into an electronic signal 50. Alternatively, when the front-end electronics 60 is implemented in an ASIC, the plurality of radiation detector elements 44 can also be mounted directly on the ASIC instead of on the PCB 46, as shown in FIG. 8. Connections between the plurality of radiation detector elements 44 and the ASIC may use bump-bonding technology while the connections between the ASIC and the PCB can use wire-bonding or any other bonding technique known in the art.

A plurality of radiation detector elements may comprise a semiconductor detector with either rectangular or circular cross section and a sensitive thickness selected on the basis of the radiation energy region relevant to the application of interest. The semiconductors that may be employed in the present invention are generally derived from, but not limited to, elements of groups III and V, e.g., GaAs, groups II and VI, e.g., CdTe, and group IV, e.g., Si, of the periodic table. Besides binary compounds and single element semiconductors, ternary materials also may be used as semiconductors capable of operating as photon-charge direct conversion devices, e.g., $Cd_{1-x}Zn_xTe$ and $Cd_{1-x}Mn_xTe$, where $0 \leq x \leq 1$. It is common practice to omit the fractional subscripts when referring to the alloy families; such practice is followed in describing the present invention. Among these semiconductors and their alloys, in one embodiment, cadmium telluride (CdTe), cadmium zinc telluride (CdZnTe), cadmium manganese telluride (CdMnTe), thallium bromide (TlBr), silicon (Si), or mercury iodide ($HgI_2$) is used. However, it will be appreciated and understood by those skilled in the art that any compound or element may be used in the present invention as long as it is capable of operating as a photon-charge direct conversion device, preferably at body temperature. In one particular embodiment, the compound semiconductor crystal used for the plurality of radiation detector elements is made from cadmium zinc telluride (CdZnTe or CZT) crystals. One skilled in the art will appreciate that the semiconductor may be larger or smaller and vary in shape depending upon the design specifications.

In one embodiment, in order to produce a sufficiently large uniform semiconductor crystals that have electrical resistivity above $10^9$ ohm-cm, the crystals are grown by using a Traveling Heater Method (THM) (or a Modified Vertical Bridgman (MVB) Method). This method eliminates the need for a complicated high-pressure chamber conventionally used in a Bridgman Method. Furthermore, the problem is resolved of lack of control of the thermal environment during growth, which results issues of melt stabilization, interface control and poor crystallinity. The MVB growth apparatus has a furnace with two primary zones. The furnace of the MVB apparatus has the upper zone for melting the crystal forming compounds, e.g., cadmium telluride and zinc telluride, and the lower zone to keep the grown crystal at a constant temperature and to limit the stress and formation of dislocations in the ingot. Although single-crystal volumes exceeding 300 $cm^3$ can be produced using this process, i.e., approximately 10 times larger than the typical single-crystal volumes from the high-pressure Bridgman method, such crystals suffer from low electrical resistivity.

In another embodiment, during the production of the compound semiconductor crystals, in order to increase the electrical resistivity of these crystals, impurities are intentionally introduced into the ingot to reduce the deleterious effects of the concentrations of native defects (i.e., cadmium vacancies and tellurium anti-sites). This way the electrical resistivity can be controllable by intentional doping with indium; however, doping the crystals with aluminum, germanium, and tin also generate a similar effect. With reference to the growth of the CZT crystals, the precise amount of indium needed to optimize electrical resistivity depends on the amount of excess tellurium used during the crystal growth process, the overpressures of cadmium, the temperature of the solidified ingot, and the thermal annealing time. Using this process, crystals with electrical resistivities above $10^{10}$ ohm-cm may be obtained, which are more than adequate for X-ray and gamma-ray detectors. Furthermore, by intentionally adding particular impurities during growth, the electron lifetimes of the compound semiconductor crystals are increased without needing to grow defect-free crystals to be used in the radiation imaging probe. These increased lifetimes lead to larger signals (i.e., current pulses) within the detector module, but much more importantly, the signal measured by the detector readout circuit is far less dependent on the location of the X-ray or gamma-ray absorption event within the crystal. As with all semiconductor detectors, the electronic noise is another important factor in determining energy resolution. The dominant source of noise typically is parallel white noise due to the dark current flowing between the detector's electrodes. In most cases, the dark current flows primarily along the surfaces of detector, rather than through the bulk of the crystal. The dark current obscures the measurement of the small current pulses generated by absorption of incident X-rays or gamma rays. The net effect is a broadening of the peaks in the energy spectrum, so it is difficult to distinguish peaks having similar energies, and nearly impossible to use the detector for identifying elements by their X-ray emissions. Hence, it is important to reduce the surface leakage current in the detectors based on II-VI semiconductor crystals. The most obvious solution, as practiced in the art, is to cool the detector by incorporating refrigerants or thermoelectric cooling stages, as well as feedback circuits for temperature stabilization. However, such approaches are undesirable because they increase the complexity and cost of the instruments. Without being bound by the theory, it has been hypothesized that one effect dominating surface leakage currents is the presence of a thin surface layer of non-stoichiometric material having an electrical resistivity much lower than the underlying crystalline substrate. If so, the detector surfaces could be passivated by one or a combination of, the three following approaches: The selective removal of the electrically active species at the surface through an etching process; Use of a chemical reaction to convert the electrically active species to a different molecular compound with desirable electrical properties (i.e., high resistivity, wide band gap, and high dielectric constant); An alternative etchant that stoichiometrically removes the damaged layer caused by cutting and polishing. In one embodiment of the present invention, the compound semiconductor crystal is further treated to achieve a passivating dielectric layer on the surface of the compound semiconductor crystals by the oxidation of the excess elemental compounds (e.g., tellurium) at the surface, which may reduce the leakage current by a factor of 10-100. In another embodiment, the compound semiconductor crystals are treated with a $NH_4F/H_2O_2$ solution, which decreases the leakage current by a factor of over 100 for most cases. Reductions in the surface leakage current after $NH_4F/H_2O_2$ passivation are a strong function of the starting conditions for the detector surfaces, i.e., duration of chemical etching, amount of time after chemical etching, surface planarity, and degree of surface oxidation. The details of the crystal treatment methods are described in the related U.S. Pat. Nos. 6,524,966 and 7,001,849, the contents of which are incorporated herein in their entirety. In addition to surface treatment, in one embodiment, the crystal is further encapsulated in a sputtered silicon nitride film. Encapsulation further extended the devices' stability, so that the detectors can be used in more long-term applications, such as space missions, unattended monitoring of stored radioactive sources, and monitoring plumes in soils.

Figure 5A:
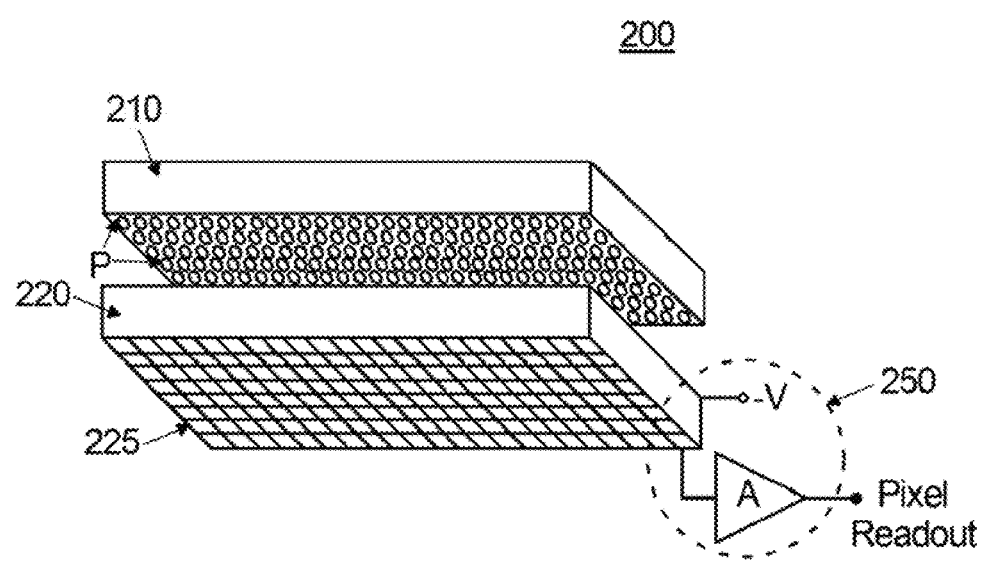
FIGS. 5A-5C illustrate a pixilated detector configuration, a bar-shaped detector array configuration, and a cross-strip detector configuration of the radiation detector, respectively.
Figure 5B:
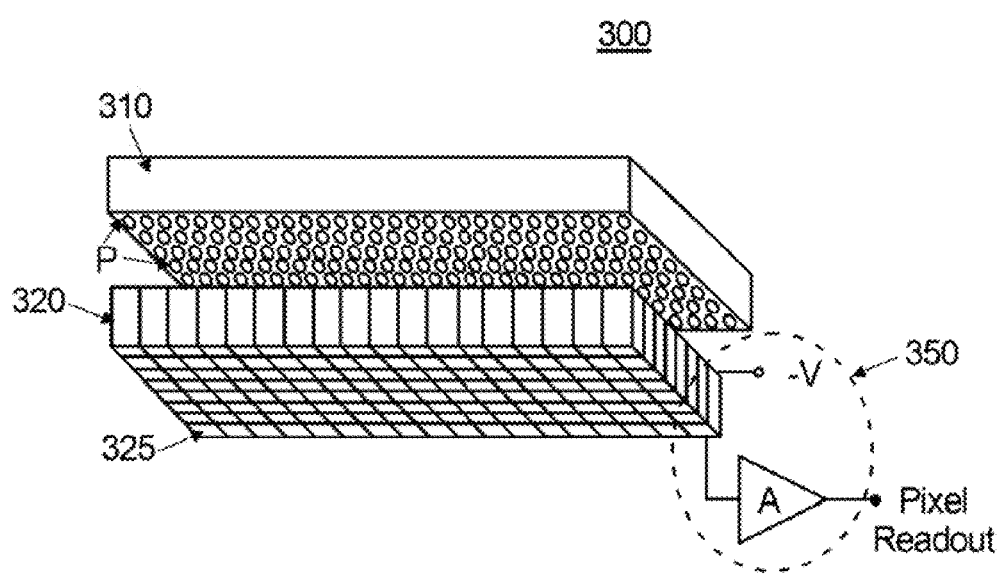
Figure 5C:
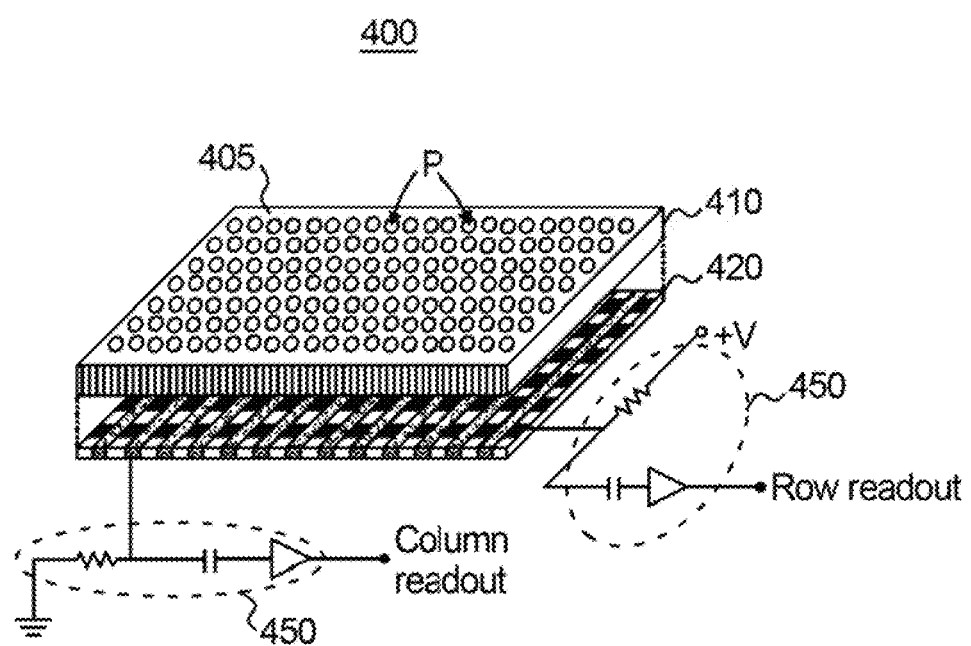

In order to localize the positions of radiation sources in an organ, e.g., prostate, different configurations of the detector's electrodes can be used, such as, but not limited to, pixilated detectors (FIG. 5A), arrays of bar-shaped detectors (FIG. 5B), and orthogonal (cross-) strip detectors (FIG. 5C). Such detectors may also be used in industrial applications where the radiation source is external to the object under study. In the latter case, the detector detects radiation passing through, or re-emitted by, the portion of the object between the detector and the radiation source.

The cathodes of all the elements can be connected together and biased by one common high voltage, or the cathodes biased at different high voltages separately. Signals are read out from the anode side from each element. In one embodiment, the detector elements in addition to a convention anode design, may have a hybrid anode. If the Frisch-grid detectors are used in the probe of the present invention, the shielding of each individual detector element has a design such as, but not limited to, pixel detectors (H. H. Barrett, et al., *Phys. Rev. Lett.* 75 (1), p. 156, 1995; incorporated herein by reference in its entirety), CAPture™ (K. Parnham, et al., in *Hard X-Ray, Gamma-Ray and Neutron Detector Physics, Proceedings of SPIE,* 1999; incorporated herein by reference in its entirety), hemispherical, (C. Szeles, et al., in *Hard X-Ray and Gamma-Ray Detector Physics VIII*, edited by Larry A. Franks, et al., *Proceedings of SPIE* Vol. 6319 (SPIE, Bellingham, Wash., 2006); incorporated herein by reference in its entirety), and Frisch-ring, (U.S. Pat. No. 6,175,120; G. Montemont, et al., *IEEE Trans. Nucl. Sci*, Vol. 48, pp. 278-281, 2001; each of which is incorporated herein by reference in its entirety). Finally, readout electronics 250 transmit the detected signal to processing and analyzing equipment in a known manner.

In one embodiment, a pixilated detector is used. FIG. 5A illustrates a radiation imaging device 200, including a collimator 210 and a detector module 220. The collimator may be designed in accordance with any of the embodiments described herein. The detector module 220 includes a pixilated detector with a common electrode on one side (e.g., cathode) and an array of sensing electrodes 225 on the other side (e.g., a plurality of anodes). Readout electronics 250 transmit the detected signal to processing and analyzing equipment.

Alternatively, an array of individual detectors may be used. FIG. 5B illustrates a radiation imaging device 300, including a collimator 310 and a detector module 320. In this embodiment, the detector module 320 includes an array of single detection elements 325. Radiation beams (not shown) substantially parallel to the axis of apertures P traverse collimator 310 and are detected by individual detection elements 325. Here, the single detection element 325 is based on semiconductor detectors with various configurations including but not limited to planar detector or the so-called Frisch-grid detector design, as proposed by A. E. Bolotnikov et al. in "*Optimization of virtual Frisch-grid CdZnTe detector designs for imaging and spectroscopy of gamma rays*", Proc. SPIE, 6706, 670603 (2007) and U.S. patent application Ser. No. 12/056,655, each of which is incorporated by reference herein in its entirety.

In yet another alternative embodiment, an orthogonal cross-strip detector is used. A cross-strip detector has one set of linear arrays of electrodes on one side, and another set of linear arrays of electrodes on the other side, oriented perpendicular to the direction of the former array. In this configuration, signals are read out from both sides and the coincidence of signals from these two sets of arrays indicates the interaction position of the gamma-ray photon inside the detector. An orthogonal strip detector may be double-sided, as proposed by J. C. Lund et al. in "*Miniature Gamma-Ray Camera for Tumor Localization*," issued by Sandia National Laboratories (August 1997) which is incorporated by reference herein in its entirety. In FIG. 5C, detector module 420 represents one possible configuration of a double-sided orthogonal strip design. In the double-sided orthogonal strip design, rows and columns of parallel electrical contacts (strips) are placed perpendicular to each other on opposite sides of the detector. Radiation detection on the detector plane is determined by scoring a coincidence event between a column and a row. More specifically, when radiation beams emitted from an object of interest traverse apertures P of collimator 410, only the radiation beams substantially parallel to the axis of the aperture P arrive at a crossing of a column and a row, to thereby generate signals on both that column and that row. Readout electronics 450 transmit the received signals to processing and analyzing equipment in a known manner.

Using the orthogonal strip design reduces the complexity of the readout electronics considerably. In general, to read out an array of $N^2$ detecting elements only requires 2×N channels of readout electronics (450 in FIG. 5C), as opposed to $N^2$ channels required for an array of N×N individual pixels. The single-sided orthogonal strip detector operates on a charge sharing principle using collecting contacts organized in rows and columns on only one side of the detector, e.g., the anode surface of a semiconductor detector. A single-sided strip detector requires even fewer electronic channels than a double-sided one. For example, whereas double-sided detectors require that electrical contacts be made to the strips on both sides, single-sided (coplanar) ones use collecting contacts arranged only on one side of the detector. In a preferred embodiment, a pixilated detector is used.

III. A COLLIMATOR

Figure 6A:
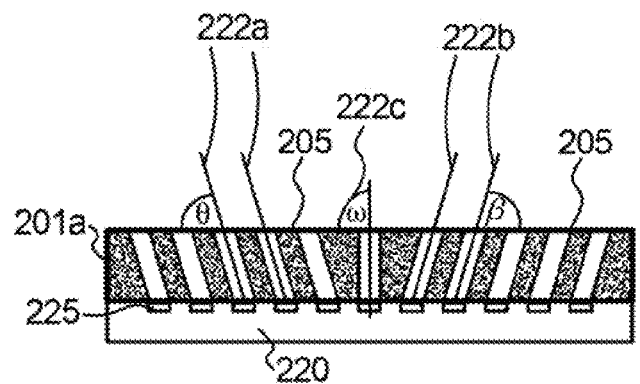
FIGS. 6A and 6B illustrate a fan beam collimator design and a focus beam collimator design, respectively.

In the radiation imaging system of the present invention (for examples see FIG. 4), the emitted radiation beams traverse the object and, if not absorbed or scattered by body tissue, for example, the beams exit the object along a straight-line trajectory. The optional collimator blocks or absorbs radiation beams that are not parallel to the axes of apertures (openings in the collimator). Radiation beams parallel to apertures are detected by the plurality of the radiation detector elements of the radiation detection module. In one embodiment, the apertures of the collimator are uniform. In another embodiment, the collimator is not uniform. Preferably, the non-uniform collimator has a fan-beam pattern of the apertures (FIG. 6A), which brings a larger field-of-view to the system. In particular, FIG. 6A illustrates a radiation detection device with a fan-beam pattern aperture collimator 201*a* and a detector module 220 with detector elements 225. The fan-beam pattern collimator 201*a* comprises a radiation-absorbing collimator body having a surface plane 205 disposed closest to a radiation source (not shown) and includes a plurality of apertures 222 (*a,b,c*) arranged throughout the collimator body. Apertures 222*a* have longitudinal axis that are arranged in a first orientation angle θ (e.g., slanted to the left in FIG. 6A) with respect to the collimator's surface plane 205.

Figure 6B:
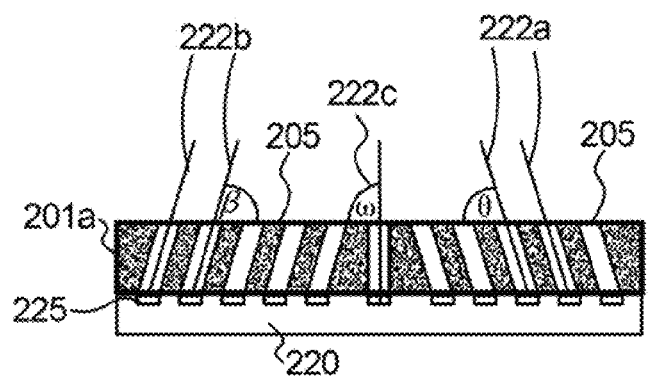

Similarly, apertures 222b have respective longitudinal axis that are arranged in a second orientation angle β (e.g., slanted to the right in FIG. 6A) with respect to the collimator's surface plane 205. Finally, apertures 222c have respective longitudinal axis that are arranged in a third orientation angle ω (e.g., perpendicular in FIG. 6A) with respect to the collimator's surface plane 205. As a result of the above-described arrangement, the apertures from these three groups bring a larger field-of-view to the system. Alternatively, the non-uniform collimator has a focus pattern of the apertures (FIG. 6B), which gives higher spatial resolution as the collimator magnifies the imaged organ. The arrangement of apertures 222 (a,b,c) is similar to the arrangement illustrated in FIG. 6A except that the apertures 222a and 222b are exchanged with each other, thus narrowing the field of view of the system.

The above-described embodiment of FIG. 2 of the present invention is directed, among other things, to balancing the tradeoff between efficiency and spatial resolution by reducing the distance between the object and the radiation detection device, so that a radiation detection device may be positioned close to, or even in contact with, the object of interest.

In a preferred embodiment, the collimator may be fabricated from a radiation-absorbing material known as a "high-Z" material, one that has high average atomic mass; high-density materials also help absorb radiation. Examples of such materials include, but are not limited to, lead (Pb), tungsten (W), gold (Au), molybdenum (Mo), and copper (Cu). The selection of the radiation-absorbing material and the thickness of the radiation-absorbent material should be determined so as to provide efficient absorption of the incident radiation, and would normally depend on the type of incident radiation and the energy level of the radiation when it strikes the surface plane of the collimator. The type of incident radiation and the energy level of the radiation depends on the particular imaging application, e.g., medical or industrial, or may be designed to be used in any of several different applications by using a general purpose radiation-absorbing material. In medical application, for instance, in one embodiment, Indium-111 ($^{111}$In; 171 keV and 245 keV) and Technetium-99m ($^{99m}$Tc; 140 keV) are used as a radioactive tracer for imaging of prostate or other organs. In such applications, it is envisioned that the collimator may be fabricated from copper, molybdenum, tungsten, lead, or gold.

In another embodiment for medical applications, Palladium-103 ($^{103}$Pd; 21 keV) is used as a radioactive implant seed for treatment of the early stage prostate cancer. In such applications, it is envisioned that the collimator may be fabricated from copper, molybdenum, tungsten, lead, or gold. In one preferred embodiment, the collimator is fabricated from copper. In another preferred embodiment, the collimator is fabricated from tungsten. In yet another preferred embodiment, the collimator is fabricated from gold. The collimator body defining the surface plane may be fabricated of a solid layer of radiation-absorbing material of a predetermined thickness, in which the plurality of apertures may be machined in any known manner according to optimized specifications. For example, a solid layer of radiation-absorbing material of a predetermined thickness may be machined in a known manner, e.g., using precision lasers, a collimator with the appropriate aperture parameters and aperture distribution pattern may be readily achieved.

The collimator body containing the plurality of apertures may also be fabricated by laterally arranging septa of radiation-absorbing material so as to form predetermined patterns of radiation-guiding conduits or channels. In addition, the collimator body having a plurality of apertures may be manufactured by vertically stacking multiple layers of radiation-absorbing material with each layer having predetermined aperture cross-sections and distribution patterns so as to collectively form radiation-guiding conduits or channels. For example, multiple layers of lead, gold, tungsten, or the like may be vertically stacked to provide enhanced absorption of stray and scattered radiation to thereby ensure that only radiation with predetermined wavelengths is detected. In the case of vertically stacking multiple layers, the collimator may be formed by stacking repetitive layers of the same radiation-absorbing material, or by stacking layers of different radiation-absorbing materials.

In the collimator, the aperture parameters such as aperture diameter and shape, aperture material, aperture arrangement, number of apertures, focal length, and acceptance angle(s) are not limited to specific values, but are to be determined subject to optimization based on required system performance specifications for the particular system being designed, as will be understood by those skilled in the art. Extensive patent and non-patent literature providing optimal configurations for apertures such as pinholes and parallel holes is readily available. Examples of such documentation are U.S. Pat. No. 5,245,191 to Barber et al., entitled Semiconductor Sensor for Gamma-Ray Tomographic Imaging System, and the journal article entitled "*Investigation of Spatial Resolution and Efficiency Using Pinholes with Small Pinhole Angle,*" by M. B. Williams, A. V. Stolin and B. K. Kundu, IEEE TNS/MIC 2002, each of which is incorporated herein by reference in its entirety.

Referring to FIG. 4, in order to reduce the overall size of a radiation imaging probe, the collimator is adapted to be positioned substantially parallel to the detector module such that the collimator may be preferably positioned close to, or even in contact with, the detector module.

Preferably, the detector module is arranged with respect to collimator so as to align each axis of aperture with the center of a corresponding detector element. In this manner, the detector module including a two-dimensional array of detector elements may be virtually divided into groups according to the orientation of the apertures within a particular group.

Figure 7A:
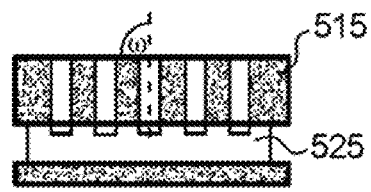
FIGS. 7A-7D illustrate exemplary designs of shielding surrounding the detector of the present invention.
Figure 7B:
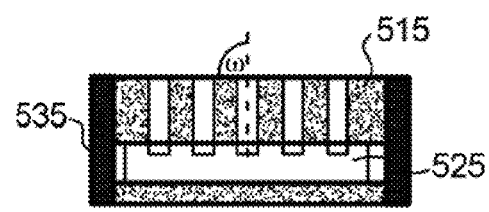
Figure 7C:
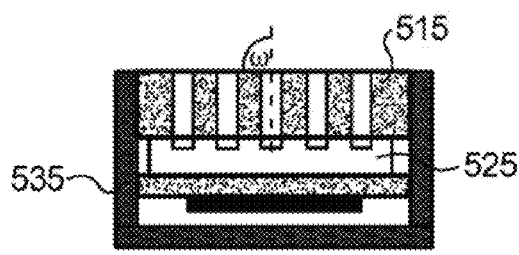
Figure 7D:
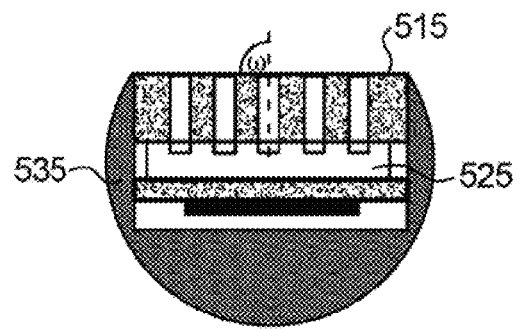

Referring now to FIGS. 7A-7D, in addition to the basic design (FIG. 7A), in a further embodiment, the collimator 515 and the radiation detector 525 can have a side shielding 535 surrounding the four (4) side surfaces of the gamma-ray detector (FIG. 7B). In yet another embodiment, back shielding 535 can also be added so that the detector is covered fully from all directions except that from which the radiation is to be detected (FIG. 7C). In these embodiments, it is envisioned that the shielding 535 have uniform rectangular shapes. However, in another embodiment, other shapes are also envisioned. For example in FIG. 7D, the shielding 535 has a piano-convex (or circular) shape on the outside surface to fit with the sheath of the probe. This design also provides better shielding with thicker materials.

IV. FRONT-END ELECTRONICS

In order to get higher spatial resolution, the pitch of detector pixels in modern imaging systems is getting smaller and smaller. As a result, the channel density increases. In this case, using an electronics readout circuit based on commercial integrated circuit and discrete elements is impractical due to the large occupied area on the PCB and the huge power consumption. In addition, the front-end circuit, which is connected to the radiation detectors directly, has to be optimized for different applications to minimize the total noise level of a specific system. Thus, design of an ASIC chip may be the best option for compact system integration, although other designs are also envisioned. The system integration in the probe of the present invention can have all the circuits on one PCB inside the probe (see FIG. 2A), or have them on different boards as long as all these boards are integrated together into one probe sheath (see FIG. 2B). FIG. 2B illustrates a design with one PCB hosting the front-end ASIC and readout control logic, while the other PCB has all the power supplies (low-voltage regulator, filters, and high-voltage generator).The readout control logic can be implemented in an ASIC, a field programmable gate array (FPGA), a Microcontroller/Microprocessor, or a combination thereof.

Figure 1B:
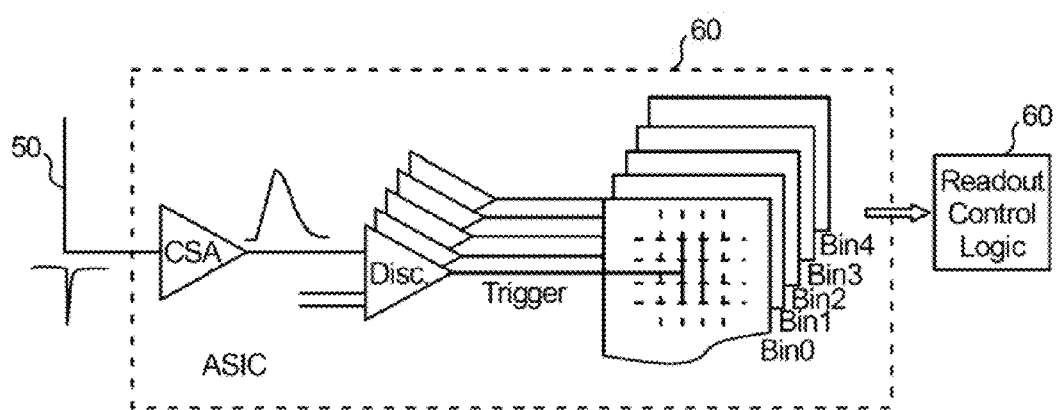
FIG. 1B illustrates a signal processing chain.

FIGS. 1A-1B illustrate the signal processing electronics 60 for the imaging system. Details are shown for only one pixel. FIG. 1A illustrates that when a photon its the active region of a pixel, it generates electron-hole pairs. The number of pairs is proportional to the energy of gamma photons With the help of high voltage bias, negatively charged carriers (electrons) will drift to the anode (pixel) inducing a current signal on it. In a preferred embodiment as shown in FIG. 1B, this signal 50 is collected and amplified by a charge sensitive amplifier (CSA) in the ASIC 60. The output signal from the CSA is compared with a preset threshold. If the signal is larger than the threshold, a trigger signal is generated, causing the counter of that channel to increase by one. Depending on the application, there can be several different thresholds, allowing the user to detect photons with different energies and produce images for each separate energy bin. Correspondingly, there are multiple energy bins (5 bins in FIG. 4) to count photons with different energies. The readout control logic reads out the values of all the energy bins of all the pixels and sends them to the computer 70 for imaging reconstruction and display.

V. IMAGE RECONSTRUCTION ALGORITHM

Figure 9A:
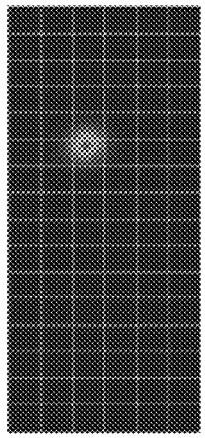
FIGS. 9A and 9B illustrate the movement of a point source in a 1-mm step to the right and a 2-mm step to the bottom.
Figure 9B:
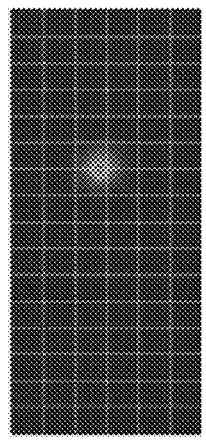

As part of the present invention, an image reconstruction library for the radiation imaging probe, e.g., prostate gamma camera, was developed. Specifically, a maximum likelihood estimation (MLE) algorithm was developed to improve the image of the radiation imaging probe. The knowledge matrix required by MLE is obtained by scanning the entire field-of-view (FOV) with a point radiation source. Because of the compound semiconductor detector's high energy resolution and high detection efficiency, it is possible to scan the entire FOV in a sub-millimeter step. Thus, the spatial resolution of the reconstructed image is improved from the pitch of the semiconductor detector, e.g., CZT detectors 2.5 mm to 1 mm. FIG. 9A shows the image of a point source Co-57, whereas, FIG. 9B shows the same source after moving 1 mm to the right and 2 mm to the bottom.

VI. APPLICATIONS/METHODS EMPLOYING THE RADIATION IMAGING PROBE

Numerous medical, industrial, scientific, environmental cleanup, and national/homeland security applications exist for the probe of the present invention. Some of the most pervasive are imaging systems for detecting and localizing tumors and other abnormalities in the body, hand-held instruments to reduce the trafficking of nuclear materials, and portable field instruments for environmental monitoring and remediation.

Application 1: Tumor Localization:

Cancer is a major cause of mortality, second only to cardiovascular disease. Almost all patients who are cured have localized disease at first presentation. Typically, patients are treated by surgery, radiotherapy, chemotherapy, or by some combination of these different methods. The success of the surgical intervention depends on the extent to which physicians can identify and then remove all of the viable cancerous cells. Anger cameras are used today in every major hospital in the United States, Western Europe, and Japan. They image a tumor after it is labeled with a nuclear medical isotope, such as technetium-99m. These conventional camera systems use large sodium-iodide scintillators and are supported by an array of up to 100 photomultiplier tubes. Theses systems weigh ~2000 pounds and have poor energy resolution. Furthermore, their performance is often restricted to counting-mode imaging in which a picture is constructed from all of the gamma rays collected by the detector; the energy spectrum is not used to generate the image. The resulting blurry images in Anger cameras are due to gamma rays that underwent scattering in the object being imaged, the media surrounding it, the aperture, and the detector itself. The problems associated with scattered radiation are so great that elaborate schemes are pursued that remove only a small portion of this noise. Some Anger cameras attempt to use counts within an energy window to discriminate object scatter. Unfortunately, the energy-resolving capability of scintillators is relatively poor, so that the scatter rejection of Anger cameras is much less than desired.

The collection of the scattered gamma rays is the root cause for the severely degraded spatial resolutions of Anger cameras. In many cases, tumors are too small to be detected with conventional technology, so there is an enormous need for an imaging system with better spatial resolution. Improvements can be achieved in the spatial resolution and in contrast by using an array of ambient temperature solid-state semiconductor detectors. The images are much superior because the detectors have a much higher linear dynamic range and can better resolve the energies of both the unscattered and scattered gamma rays, thereby allowing easy subtraction of the scattered gamma rays from the displayed image.

To address these applications, the instant inventors have fabricated arrays of cadmium zinc telluride detectors and incorporated them into gamma cameras for medical diagnostics. The excellent energy resolution and the efficiency of the detector arrays produced from cadmium zinc telluride (with Zn composition, 0~20%) provide a unique, viable means for producing high-quality images.

Application 2: Imaging of Prostate Tumors:

According to the American Cancer Society, in the United States, about one in six men will be diagnosed with prostate cancer over their lifetime. It is one of the most common cancers among males and the Number 2 killer, after lung cancer. This year, approximately 186,000 American men will be diagnosed for the first time with prostate cancer; about 29,000 will die from the disease. Treating prostate cancer is a balancing act, because there is no one treatment suitable for all. The main types of treatments are surgical removal of the gland, radiation, and implanting radioactive seed. Each treatment has serious side effects, the most troublesome being sexual dysfunction and urinary and bowel incontinence. Several studies suggest that often such treatments are overused. Unnecessary treatments usually result from the wide variability of these cancers and the difficulties in effectively diagnosing and characterizing the cancerous tissue. This is particularly true for small, non-aggressive early-stage cancers that almost always are difficult to reliably detect with conventional ultrasound techniques.

The probe of the present invention affords creative ways to overcome many problems with ultrasound techniques by providing a new nuclear-medical imaging tool for the earlier detection of small tumors and for the image-guided biopsy of suspect tissues. The value of this instrument rests upon the performance enhancements described in this application, which now allow the production and utilization of high-quality semiconductor, e.g., CZT, detector arrays for gamma imaging. The semiconductor imaging arrays of the present invention also address the problems of conventional cancer imaging instruments in the following important ways: (1) the prostate-cancer imaging system utilizes a small probe with a detector volume of about $4(L)\times1.5(W)\times0.5(H)$ cm$^3$, making it competitive with ultrasound detection systems; (2) very small, low-power circuits were designed to reduce the heat dissipation in the probe, enable the compact packaging of the probe, and eliminate the need for a cumbersome cooling system, so that the probe is small enough to insert into the rectum; and (3) by using a trans-rectal probe, the imaging detector array can be very close to the prostate gland, thereby greatly increasing its efficiency in detecting and imaging the gamma rays emitted from the radioactive tracer(s), e.g., Indium-111 or other gamma emitting isotope, taken up in the gland as compared to large Anger cameras placed outside the body.

Application 3: Diagnosis of Heart Disease:

Medical systems for this application are similar to the one discussed above for cancer detection. After injecting a radiotracer containing, for example, technetium-99m into the blood flow and by examining the specific gamma emissions of the radiotracer, regions of the heart with lower than expected blood flow can be identified. Similarly, radiopharmaceuticals can be employed in bone scans, identifying regions with abnormalities and the presence of lesions.

Application 4: Safeguarding of Nuclear Materials and Weapons:

Large inventories of Special Nuclear Materials (SNM) exist in former communist-block countries, Europe, the United States, and possibly the Middle East and Africa. Because the quantities required to produce a device with nuclear yield are relatively small, concealment and transport of special nuclear materials can be somewhat easily achieved, and conventional security measures (video surveillance, human inspection, etc.) are neither fully adequate nor reliable. One approach to solve this problem is to monitor and safeguard nuclear materials by detecting their characteristic gamma-ray emissions. Depending on the material and its isotopic compositions, gamma rays with isotope-specific energies are emitted. To assure acceptable numbers of false alarms and identify isotopes, it is imperative to have an energy-resolving capability in the detection system. Although cryogenically cooled detectors such as high purity germanium offer adequate gamma-ray resolution, the need to replace the cryogen periodically and the relatively large volumes and weights limit the uses of germanium detectors in field applications, particularly if long-term operation is desired. New compact ambient semiconductor (e.g., CZT) detectors overcome some of the major limitations inherent in both cryogenic- and scintillator-based spectrometer systems. Because neither cryogen nor photomultiplier tubes are needed, the systems occupy much less space and are ideally suited for many portable applications, particularly those requiring both enhanced energy resolution and unattended operation. Because of the low power required to operate the sensors, battery-operated instruments were recently built by the inventors and others for precisely identifying and monitoring of nuclear materials in the field.

Application 5: Spectrometers and Imagers for Cleanup of Radioactive and Mixed Waste:

Gamma-ray spectrometers and imaging cameras based on the semiconductor detectors can also be used to characterize radioactive sources distributed in the environment. The Department of Energy, for example, hopes to characterize 55-gallon radioactive and mixed-waste containers to ensure that the contents are not leaking, and, in some cases, to determine what is inside without undertaking detailed laboratory analyses or generating secondary wastes. The Department of Energy has roughly one million such containers. The imaging instrument of the present invention has the spatial resolution sufficient for imaging radioactive waste, and much better spatial resolutions are feasible by using different collimation designs. Full characterization is essential before safe, effective, and efficient remediation strategies can be planned and executed.

Application 6: Real-Time Dosimeters:

The semiconductor sensors can provide an indicator of radiological hazards for emergency response workers, such as firemen and policemen. The size of an entire battery-operated, low-cost system has to be no larger than a beeper, and provide warnings to untrained personnel of enhanced dangerous radiation levels and doses. Other agencies (e.g., customs agents and postal workers) could use it to assist with interdiction of a wide range of radioactive materials.

Application 7: X-Ray Radiography:

A linear array of semiconductor detectors can be constructed to provide high-spatial-resolution X-ray transmission images. Here, transmission images are generated by translating a sample between a fan-shaped X-ray beam and a linear array of detectors at a controlled speed (e.g., baggage moving along a conveyor belt). The current size of the linear arrays is limited to several inches, and the systems cannot image large containers without a step-and-repeat process.

Application 8: Oil Exploration:

Oil well logging relies heavily on neutron sources to activate elements within the earth's composition and detectors to analyze the gamma-ray emissions and determine the specific elements present. For example, the characteristic gamma-ray emission of hydrogen and carbon can reveal the presence of hydrocarbons in a bore hole. In this application, the gamma-ray detectors must be compact to fit in the well (i.e., no cumbersome cryogenic cooling apparatus), have a high energy resolution for gamma ray energies in the 2-8 MeV energy range, and possess good efficiency to allow rapid collection of data as a function of depth. To meet these requirements, a large mosaic array of semiconductor gamma-ray detectors must be constructed. This can be done via the principal design of the present invention by fabricating a plurality of virtual Frisch-grid arrays, low-power compact readout electronics, pulse-height correction for each gamma-absorption event, coupling individual detectors into modules with independent readout electronic channels, and building modules into the suitable array for the specific application.

Application 9: X-Ray Fluorescence Instruments for Materials Sorting:

The detectors of the present invention (e.g., based on CZT) can precisely identify elements based on their characteristic X-ray fluorescence emissions and provide detailed quantitative information about the composition of unknown materials. The ability to quantify most elements within the periodic table based on their X-ray fluorescence is important to a wide range of users who need to identify unknown materials. Users range from the front-end suppliers of raw materials, through the fabricators and customers of end-products to the scrap dealers.

The elemental components are quantified by their specific X-ray emissions when they are excited by a source (e.g., gamma-emitting isotope). The gamma-ray source can be contained in a compact (few cm$^3$) probe. The principal advantage of the detectors of present invention is that they offer high-resolution X-ray spectroscopy at room temperature. Previously, X-ray fluorescence analysis was largely confined to laboratory environments because of the maintenance requirements of the cryogenically cooled lithium-drifted silicon X-ray detectors. With reductions in the leakage currents of the semiconductor crystal devices, the performance of the detectors for low-energy X-rays was greatly enhanced, allowing them to operate at ambient temperatures. This capability, coupled with a performance almost as good as a cooled silicon detector supports the manufacturing of X-ray fluorescence instruments that are much more compact, lightweight, and require significantly less attention. Some specific field applications include the analysis of lead in paints, measurement of environmental toxins, recycling of metals (e.g., aluminum, brass-bronze-nickel, and stainless steel alloys), and environmental cleanup operations.

VII. EXAMPLES

Figure 2C:
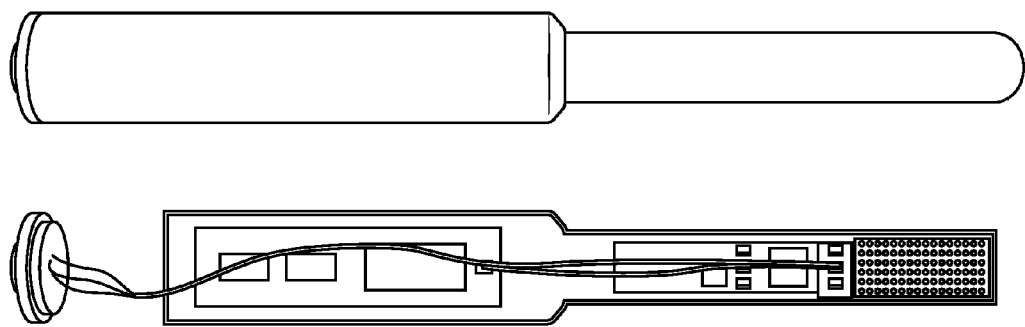
FIG. 2C illustrates an exemplary embodiment of the probe reduced to practice.
Figure 3:
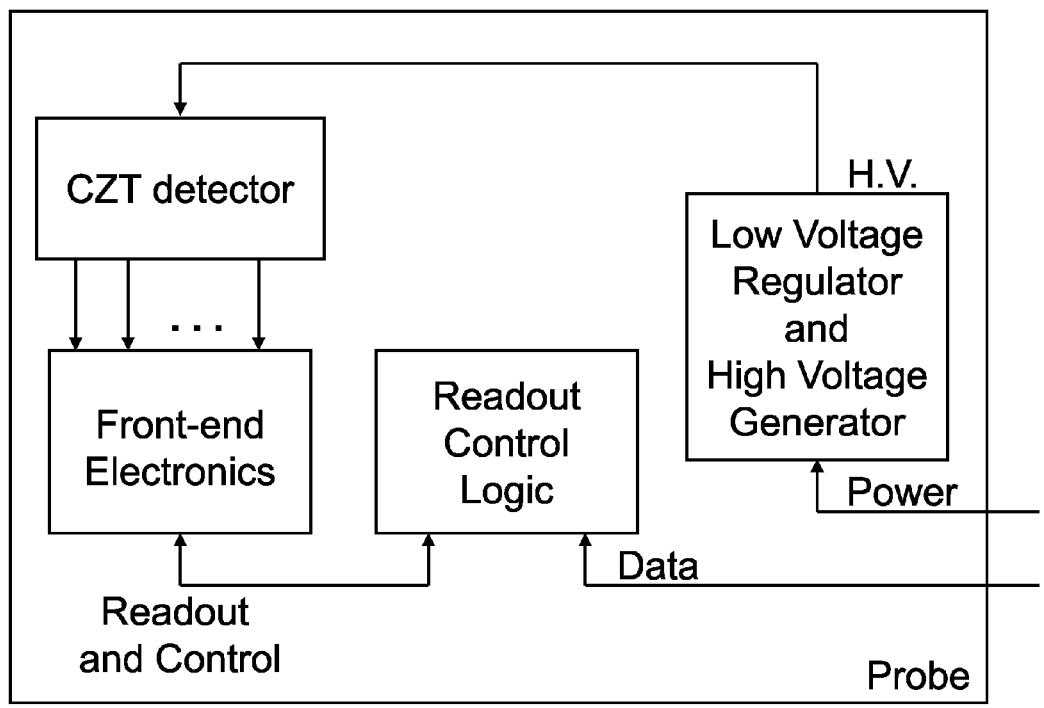
FIG. 3 illustrates a block diagram of the probe shown in FIG. 1A.

A compact radiation imaging probe with a volume of about 30(L)×2.5(W)×2.5(H) $cm^3$ was constructed, making it comparable to ultrasound detection systems. Internally, the probe includes detector module made with a tungsten collimator, a pixilated detector fabricated with a CZT crystal, and ASIC circuitry. The ASIC circuitry was optimized to have 64 channels so that it can be integrated right underneath the CZT detectors to readout an 8×8 pixel array and reduce the size of the probe. This ASIC is a low power design, consuming about 300 mW of power. Thus, no extra cooling apparatus is needed. Even if the system runs for hours, the dissipated heat won't degrade the image quality. In addition, the ASIC had multiple energy thresholds, which allowed for simultaneous counting of gamma photons in several different energy windows. This feature enabled the probe to distinguish the real photon events from the low energy or high energy background, or to acquire separate images of different radioactive tracers (emitting photons with different energy) from different radiopharmaceuticals simultaneously. FIG. 2C shows the integration of this ASIC with pixilated CZT detector in a prostate gamma probe embodiment of the present invention. The profile of the PCB is limited by the CZT detector, not electronics circuit. Thus, the size of the finished probe is optimized based on the size of the detector. FIGS. 9A and 9B illustrate the images of a radiation source acquired by this camera. In these figures, the radiation source moves in a step of 1 mm to the right and 2 mm to the bottom. FIG. 9A illustrates the image before the movement and FIG. 9B illustrates the image after the movement. The grids in these figures indicate the size of pixels, 2.5×2.5 $mm^2$.

All publications and patents mentioned in the above specification are herein incorporated by reference. Various modifications and variations of the described probe and its components will be apparent to those skilled in the art without departing from the scope and spirit of the invention. Although the disclosure has been described in connection with specific preferred embodiments, it should be understood that the invention as claimed should not be unduly limited to such specific embodiments. Indeed, those skilled in the art will recognize, or be able to ascertain using no more than routine experimentation, many equivalents to the specific embodiments of the invention described herein. Such equivalents are intended to be encompassed by the following claims.

The invention claimed is:

1. A radiation imaging probe contained within a probe sheath, comprising:
   a plurality of semiconductor detectors configured as an orthogonal strip detector;
   a signal processing circuit attached to the plurality of semiconductor detectors to read out and process the signal produced by the detectors due to an absorption of the radiation; and
   a power supply and associated power supply circuits;
   wherein the plurality of semiconductor detectors is operable to detect x-ray or gamma ray radiation.

2. A radiation imaging probe contained within a probe sheath, comprising:
   a plurality of semiconductor detectors configured in an array of individual detectors;
   a signal processing circuit attached to the plurality of semiconductor detectors to read out and process the signal produced by the detectors due to an absorption of the radiation; and
   a power supply and associated power supply circuits;
   wherein the array of individual detectors is a virtual Frisch-grid detector array; and
   wherein the plurality of semiconductor detectors is operable to detect x-ray or gamma ray radiation.

3. A radiation imaging probe contained within a probe sheath, comprising:
   a plurality of semiconductor detectors wherein each of the plurality of semiconductor detectors include a semiconductor made from a compound of elements of groups III and V of the periodic table, of elements of groups II and VI of the periodic table, and of elements or alloys of group IV of the periodic table;
   a signal processing circuit attached to the plurality of semiconductor detectors to read out and process the signal produced by the detectors due to an absorption of the radiation; and
   a power supply and associated power supply circuits;
   wherein the plurality of semiconductor detectors is operable to detect x-ray or gamma ray radiation.

4. The radiation imaging probe of claim 3, where the semiconductor is a single element crystal.

5. The radiation imaging probe of claim 3, wherein the semiconductor is a binary compound.

6. The radiation imaging probe of claim 3, wherein the semiconductor is a ternary compound or alloy.

7. The radiation imaging probe of claim 3, wherein the semiconductor comprises CdZnTe, CdTe, CdMnTe, $HgI_2$, or TlBr.

8. The radiation imaging probe of claim 7, wherein the semiconductor is CdZnTe.

9. A radiation imaging probe contained within a probe sheath, comprising:
   plurality of semiconductor detectors;
   a collimator positioned on top of the plurality of semiconductor detectors;
   a signal processing circuit, including a front-end electronic implemented as an application-specific integrated circuit (ASIC), attached to the plurality of semiconductor detectors to read out and process the signal produced by the detectors due to an absorption of the radiation; and
   a power supply and associated power supply circuits;
   wherein the plurality of radiation detectors is mounted directly on the ASIC; and
   wherein the plurality of semiconductor detectors is operable to detect x-ray or gamma ray radiation.

10. The radiation imaging probe of claim 9, wherein connections between the semiconductor detector and ASIC use bump-bonding.

* * * * *